US006919208B2

(12) United States Patent
Levy et al.

(10) Patent No.: US 6,919,208 B2
(45) Date of Patent: Jul. 19, 2005

(54) METHODS AND COMPOSITIONS FOR ENHANCING THE DELIVERY OF A NUCLEIC ACID TO A CELL

(75) Inventors: Robert J. Levy, Merion Station, PA (US); Peter L. Jones, Denver, CO (US); Quanyi Li, Westmont, NJ (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 302 days.

(21) Appl. No.: 09/851,327

(22) Filed: May 9, 2001

(65) Prior Publication Data

US 2002/0034821 A1 Mar. 21, 2002

Related U.S. Application Data

(60) Provisional application No. 60/206,143, filed on May 22, 2000.

(51) Int. Cl.[7] ........................ C12N 15/63; C12N 15/88; C12Q 1/68
(52) U.S. Cl. ........................ 435/455; 435/6; 435/320.1; 435/456
(58) Field of Search ............................ 435/6, 455, 456, 435/320.1; 514/44; 424/93.2

(56) References Cited

FOREIGN PATENT DOCUMENTS

WO  WO 99/34831 A1  7/1999
WO  WO 01/51092 A2  7/2001

OTHER PUBLICATIONS

Schneider et al. "Targeted gene delivery into alpha–9 beta–1–integrin–displaying cells by a synthetic peptide," FEBS Letters 458 (3): 329–332, Sep. 24, 1999.*
Shih et al., "Matrigel treatment of primary hepatocytes following DNA transfection enhances responsiveness to extracellular stimuli," Biotechniques 18 (5): 813, 814, 816, May 1995.*
Grant et al., "Matrigel induces thymosin beta–4 gene in differentiating endothelial cells," J. Cell Sci. 108 (Pt. 12): 3685–3694, Dec. 1995.*
Watanabe et al., "Highly efficient transfection into primary cultured mouse hepatocytes by use of cation–liposomes: an application for immunization," J. Biochem. 116 (6): 1220–1226, Dec. 1994.*
Pasco et al., "Efficient DNA–mediated gene transfer into primary cultures of adult rat hepatocytes," DNA 8 (7): 535–541, Sep. 1989.*
Orkin et al. "Report and recommendations of the panel to assess the NIH investment in research on gene therapy," issued by US National Institutes of Health, Bethesda, MD, Dec. 7, 1995.*

Fasbender, et al., "Complexes of Adenovirus with Polycationic Polymers and Cationic Lipids Increase the Efficiency of Gene Transfer in Vitro and in Vivo," *The Journal of Biological Chemistry*, vol. 272, No. 10, pp. 6479–6489 (1997), The American Society for Biochemistry and Molecular Biology, Inc., USA.

Uhlmann, et al., "Chemical Reviews," *Antisense Oligonucleotides: A New Therapeutic Principle*, vol. 90, No. 4, pp. 544–584 (1990), The American Chemical Society, USA.

Schneider, et al., "Building Blocks for Oligonucleotide Analogs with Dimethylene–Sulfide,–Sulfoxide, and –Sulfone Groups Replacing Phosphodiester Link Ages," Tetrahedron Letters, vol. 31, No. 3, pp. 335–338 (1990), Pergamon Press plc, UK.

Low, et al., "Complete amino acid sequence of bovine thymosin $\beta_4$: A thymic hormone that induces terminal deoxynucleotidyl transferase activity in thymocyte populations," *Proc. Natl. Acad. Sci.*, vol. 78, No. 2, pp. 1162–1166, (1981), Immunology, USA.

Safer, et al., "Isolation of a 5–kilodalton actin–sequestering peptide from human blood platelets," *Proc. Natl. Acad. Sci.*, vol. 87, pp. 2536–2540, (1990), Cell Biology, USA.

Low, et al., "Thymic Hormones and Peptides," *Methods in Enzymology*, vol. 116, pp. 248–255, (1985), Academic Press, USA.

Nachmias, et al., "Small actin–binding proteins: the β–thymosin family," *Cell Biology*, vol. 5, pp. 56–62 (1993), Current Biology Ltd, USA.

Bradke, et al., "The Role of Local Actin Instability in Axon Formation," *Science*, vol. 283, pp. 1931–1934 (1999), American Association for the Advancement of Science, USA.

Cooper, et al., "Effects of Cytochalasin and Phalloidin on Actin," *The Journal of Cell Biology*, vol. 105, pp. 1473–1478, (1987) The Rockefeller University Press, USA.

Orkin, et al., "Report and Recommendations of the Panel to Assess the NIH Investment in Research on Gene Therapy," pp. 1–49 (1995), National Institute of Health, USA.

(Continued)

*Primary Examiner*—Scott D. Priebe
(74) *Attorney, Agent, or Firm*—Dann, Dorfman, Herrell and Skillman

(57) ABSTRACT

The present invention relates to methods and compositions useful for enhancing the efficiency of delivery of a nucleic acid to a cell. Preferably the cell is a mammalian cell. The method comprises providing to a cell an agent capable of enhancing the cytoskeletal permissiveness of the cell for transfection. The method also comprises providing to the cell a nucleic acid delivery system for the transfection of the cell, whereby the efficiency of delivery of a nucleic acid to the cell is enhanced. Compositions and kits for enhancing the efficiency of delivery of a nucleic acid to a cell are also included

10 Claims, 7 Drawing Sheets

OTHER PUBLICATIONS

Indar, et al., "Current concepts in immunotherapy for the treatment of colorectal cancer," *J.R. Coll. Edinb.*, vol. 47, pp. 458–474 (2002), The Royal College of Surgeons of Edinburgh, Great Britain.

De Kleijn, et al., "Biological therapy of colorectal cancer," *European Journal of Cancer*, vol. 38, pp. 1016, 1022 (2002), Pergamon Press, The Netherlands.

Behr, et al., "Radioimmunotherapy of Small–Volume Disease of Metastatic Colorectal Cancer," *Cancer*, vol. 94, No. 4, pp. 1373–1381 (2002), American Cancer Society, USA.

Stein, et al., "Combining Radioimmunotherapy and Chemotherapy for Treatment of Medullary Thyroid Carcinoma," *Cancer*, vol. 94, No. 1, pp. 51–61 (2002), American Cancer Society, USA.

Behr, et al., "Improved Treatment of Medullary Thyroid Cancer in a Nude Mouse Model by Combined Radioimmunotherapy: Doxorubicin Potentiates the Therapeutic Efficacy of radiolabeled Antibodies in a Radioresistant Tumor Type," *Cancer Research*, vol. 57, pp. 5309–5319 (1997), American Association for Cancer Research, USA.

Stein, et al., "Carcinoembryonic Antigen as a Target for Radioimmunotherapy of Human Medullary Thyroid Carcinoma: Antibody Processing, Targeting, ad Experimental Therapy with $^{131}$I and $^{90}$Y Labeled Mabs," *Cancer Biotherapy & Radiopharmaceuticals*, vol. 14, No. 1, pp. 37–47 (1999), Mary Ann Liebert, Inc., USA.

Kinuya, et al., "Efficacy, toxicity and mode of interaction of combination radioimmunotherapy with 5–fluorouacil in colon cancer xenografts," *J Cancer Res Clin Oncol*, vol. 125, pp. 630–636 (1999), Springer–Verlag, Germany.

Juweid, et al., "Phase I/II Trial of $^{131}$I–MN–14 (F(ab)$_2$ Anti–Carcinoembryonic Antigen Monoclonal Antibody in the Treatment of Patients with Metastatic Medullary Thyroid Carcinoma," *American Cancer Society*, vol. 85, pp. 1828–1842, (1999).

Juweid, et al., "Prospects of Radioimmunotherapy in Epithelial Ovarian Cancer: Results with Iodine–131–Labeled Murine and Humanized MN–14 Anti–carcinoembryonic Antigen Monoclonal Antibodies[1]," *Gynecologic Oncology*, vol. 67, pp. 259–271 (1997) Article No. G0974870, Academic Press, USA.

Spiller, et al., "Improving the Intracellular Delivery and Molecular Efficacy of Antisense Oligonucleotides in Chronic Myeloid Leukemia Cells: A Comparison of Streptolysin–O Permeabilization, Electroporation, and Lipophilic Conjugation," *Blood*, vol. 91, No. 12, pp. 4738–4746 (1996), The American Society of Hematology, USA.

Muhlrad, et al., "Dynamic Properties of Actin," *The Journal of Biological Chemistry*, vol. 269, No. 16, pp. 11852–11858 (1994), The Journal of Biological Chemistry, USA.

Wang, et al., "Cellular Factors Mediate Cadmium–Dependent Actin Depolymerization," *Toxicology and Applied Pharmacology*, vol. 139, pp. 115–121 (1996), Academic Press, Canada.

* cited by examiner

Native collagen

Denatured collagen

Native collagen +GFP DNA

Denatured collagen+GFP DNA

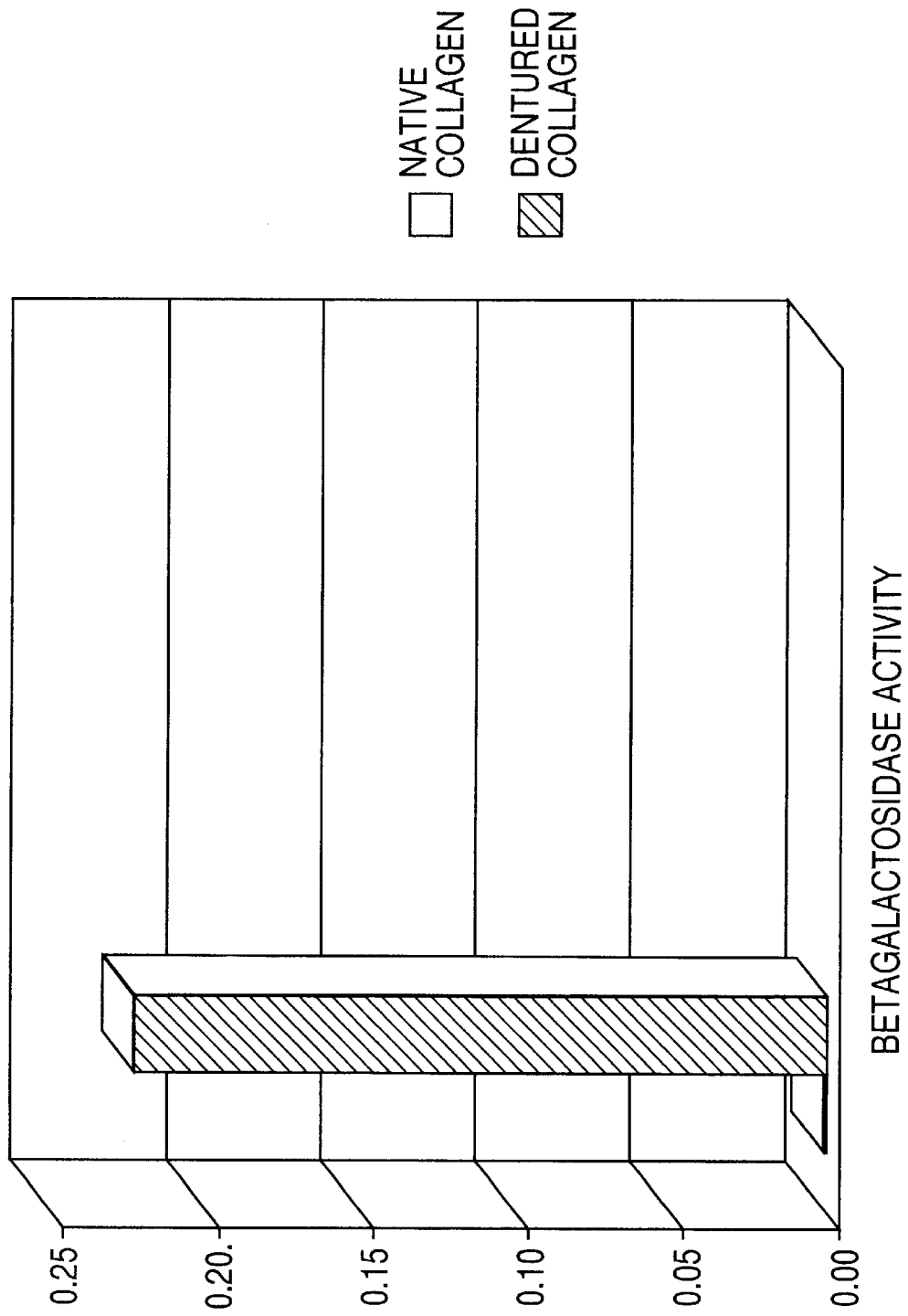

Collagen (No TNC)

TNC-15.0µg/ml

TNC-50.0 µg/ml

TNC- 15.0µg/ml

METHODS AND COMPOSITIONS FOR ENHANCING THE DELIVERY OF A NUCLEIC ACID TO A CELL

This application claims priority to U.S. Provisional Application No. 60/206,143 filed May 22, 2000.

STATEMENT REGARDING FEDERALLY SUPPORTED RESEARCH AND DEVELOPMENT

This invention was supported in part by U.S. Government finds (NIH Grant No. HL 38118), and the U.S. Government may therefore have certain rights in the invention.

BACKGROUND OF THE INVENTION

Gene therapy is generally understood to refer to techniques designed to deliver nucleic acids, including antisense DNA and RNA, ribozymes, viral fragments and functionally active therapeutic genes into targeted cells (Culver, 1994, Gene Therapy: A Handbook for Physicians, Mary Ann Liebert, Inc., New York, N.Y.). Such nucleic acids may themselves be therapeutic, as for example antisense DNAs that inhibit mRNA translation, or they may encode, for example, therapeutic proteins that promote, inhibit, augment, or replace cellular functions.

A serious shortcoming of current gene therapy strategies, including both ex vivo and in vivo gene therapy methods, is the inability of previously described vector and delivery system combinations to deliver nucleic acids efficiently into the interior of cells of a targeted population. In December, 1995, the U.S. National Institutes of Health issued a "Report and Recommendations of the Panel to Assess the NIH Investment in Research on Gene Therapy" (Orkin et al., 1995, National Institutes of Health, Bethesda, Md.). In this Report, it was recognized that the development of gene therapy approaches to disease treatment was being inhibited, in part, by a dearth of effective gene transfer vectors. The Report recognized a need for further research applied to improving vectors for gene delivery.

Numerous compositions and methods are known for delivering a nucleic acid to an animal tissue. Such compositions include "naked" (i.e. non-complexed) nucleic acids, nucleic acids complexed with cationic molecules such as polylysine and liposome-forming lipids, and virus vectors.

Naked nucleic acids can be taken up by various animal cells, but are subject to nucleolysis, both inside and outside of cells that take them up. For example, it is known that cells in wounded tissue (e.g. cells lining an incision made in a tissue) are particularly amenable to taking up naked nucleic acids. Examples of such cells include, but are not limited to, fibroblasts, capillary endothelial cells, capillary pericytes, mononuclear inflammatory cells, segmented inflammatory cells, and granulation tissue cells.

The use of nucleic acid analogs which are relatively resistant to nucleolysis is known. Such analogs include, for example, phosphorothioate nucleic acid analogs. However, in some situations, particularly where incorporation of the nucleic acid into the genome of the target cell is desired, the use of nucleic acid analogs can be undesirable. Targeting of naked nucleic acid vectors to particular animal tissues can be difficult, particularly in situations in which the tissue is normally bathed by a liquid in which the vector may be carried away from the tissue site.

Compositions for sustained release of naked nucleic acids are known, but such compositions have many of the same drawbacks of other naked nucleic acid vectors, namely, that the nucleic acids released from the compositions may not be efficiently taken up by cells of the desired tissue and that the nucleic acids released from the compositions are susceptible to nucleolysis. Examples of such compositions include compositions comprising naked nucleic acids in a biodegradable polymer matrix. Another shortcoming of such compositions is that it is difficult to target them to specific tissues in order to achieve localized delivery of the nucleic acid. Such compositions generally occur in liquid form, which must be injected at the desired site, but is capable of flowing from the site of administration to other sites.

Numerous vectors comprising a nucleic acid complexed with a compound to improve stability or uptake of the nucleic acid by a target cell have been described. Such compounds include, by way of example, calcium phosphate, polycations such as diethylaminoethyl-dextran, polylysine, or polybrene, and liposome-forming lipids such as didocyl-methylammonium bromide and Lipofectamine®. Many of these compounds are toxic or produce undesired reactions when administered to patients. Thus, while nucleic acid vectors comprising a nucleic acid complexed with one of these compounds may be useful for transfection of cultured cells, these vectors are not useful for delivering nucleic acids to cells in an animal tissue.

Virus vectors are generally regarded as the most efficient nucleic acid vectors. Recombinant replication-defective virus vectors have been used to transduce (i.e., infect) animal cells both in vitro and in vivo. Such vectors have included retrovirus, adenovirus, adeno-associated virus vectors, and herpesvirus vectors. While highly efficient for gene transfer, a major disadvantage associated with the use of virus vectors is the inability of many virus vectors to infect non-dividing cells. Another serious problem associated with the use of virus gene vectors is the potential for such vectors to induce an immune response in a patient to whom they are administered. Such an immune response limits the effectiveness of the virus vector, since the patient's immune system rapidly clears the vector upon repeated or sustained administration of the vector. Furthermore, insertion of a gene into the genome of a cell by a virus vector may induce undesirable mutations in the cell. Other problems associated with virus gene vectors include the inability to appropriately regulate gene expression over time in transfected cells, the potential production and transmission to other humans of harmful virus particles, local and general toxicity, undesirable immunogenicity, and unintended disruption of target or other cell metabolism.

Despite the development of the techniques discussed above, there remains a need in the art for methods and compositions which can be used to enhance the delivery of a nucleic acid to a desired cell which is to be transfected with the nucleic acid. The present invention meets this need.

BRIEF SUMMARY OF THE INVENTION

The invention includes a method of enhancing the efficiency of delivery of a nucleic acid to a cell. The method comprises a) providing to the cell an agent capable of enhancing the cytoskeletal permissiveness of the cell for transfection in an amount effective to enhance the cytoskeletal permissiveness; and b) providing to the cell a nucleic acid delivery system for the transfection of the cell, whereby the efficiency of delivery of a nucleic acid to the cell is enhanced.

In one aspect, the agent is an isolated nucleic acid encoding a protein or a polypeptide, wherein the protein or the polypeptide when expressed in the cell is capable of enhancing the cytoskeletal permissiveness of the cell for transfection.

In another aspect, the nucleic acid delivery system is provided to the cell simultaneously with providing the agent.

In one embodiment, the nucleic acid delivery system is provided to the cell prior to providing the agent.

In another embodiment, the nucleic acid delivery system is provided to the cell after providing the agent.

In yet another embodiment, the agent is denatured collagen or a peptide thereof.

In a further embodiment, the agent is Thymosin beta-4 (TB4) or a peptide thereof.

In one aspect, the agent is Tenascin C or a peptide thereof.

In another aspect, the agent comprises Tenascin C and TB4.

In one embodiment, the protein is one or more of Tenascin C, TB4 and peptides thereof.

In another embodiment, the isolated nucleic acid is provided to the cell using a vector selected from the group consisting of a plasmid vector, a viral vector, and a linearized nucleic acid.

In a further embodiment, the nucleic acid delivery system comprises a vector selected from the group consisting of a plasmid vector, a viral vector, and a linearized nucleic acid.

In one aspect of the method of the invention, enhancing the cytoskeletal permissiveness for transfection comprises inhibiting DNAase I activity in the milieu surrounding or the cytoplasm of the cell.

In another aspect, enhancing the cytoskeletal permissiveness for transfection comprises reducing the overall electronegative charge of the milieu surrounding or the cytoplasm of the cell to be transfected.

In one aspect, enhancing the cytoskeletal permissiveness comprises enhancing the level of G-Actin in the cell.

In another aspect, enhancing the level of G-Actin comprises depolymerizing F-Actin to G-Actin.

In one embodiment, the agent is a compound capable of modulating an ion channel in the cell.

In another embodiment, the agent is an actin binding protein.

In a further embodiment, the agent is a compound capable of rendering G-Actin less susceptible to proteolysis upon binding with G-Actin.

In one aspect, the compound is selected from the group consisting of beryllium fluoride and a cadmium salt.

In one embodiment, the level of G-Actin is enhanced by directly or indirectly upregulating TB4.

In one aspect, the TB4 is indirectly upregulated by growing the cell on a Tenascin C inducing substrate.

In one embodiment, the Tenascin C inducing substrate is denatured collagen or a peptide thereof.

In a further embodiment, the agent is a modulator of an intermediate in the Tenascin C and TB4 receptor-signaling pathway.

In a still further embodiment, the agent is a cytochalasin.

In yet another embodiment, the agent is selected from the group consisting of a TB4 promoter, a molecule which participates in cell—cell interactions, a molecule which participates in cell—cell adhesion, and a synthetic extracellular matrix molecule having design features effective to enhance the cytoskeletal permissiveness of a cell for transfection.

The invention also includes a composition for enhancing the efficiency of delivery of a nucleic acid to a cell. The composition comprises a) an agent capable of enhancing the cytoskeletal permissiveness of the cell for transfection in an amount effective to enhance the permissiveness; and b) a nucleic acid delivery system for the transfection of the cell.

In one embodiment, the nucleic acid delivery system is selected from the group consisting of a plasmid vector, a viral vector, and a linearized nucleic acid.

In one aspect, the agent is an isolated nucleic acid encoding a protein or a polypeptide, wherein the protein or the polypeptide when expressed in the cell is capable of enhancing the cytoskeletal permissiveness of the cell for transfection.

In another aspect, the isolated nucleic acid is a component of a nucleic acid delivery system.

In one embodiment, the polypeptide is selected from the group consisting of TB4, Tenascin C and peptides thereof.

In another embodiment, the agent is selected from the group consisting of TB4 or a peptide thereof, Tenascin C or a peptide thereof, an actin depolymerization agent, a cytochalasin, a modulator of TB4, a modulator of an intermediate in the Tenascin C and TB4 receptor-signaling pathway, a nuclease inhibitor and denatured collagen or a peptide thereof.

The invention also includes a kit for enhancing the efficiency of delivery of a nucleic acid to a cell. The kit comprises a) an instructional material; b) an agent capable of enhancing the cytoskeletal permissiveness of a cell for transfection in an amount effective to enhance the permissiveness; and c) a nucleic acid delivery system.

BRIEF DESCRIPTION OF THE DRAWINGS

The foregoing summary, as well as the following detailed description of the invention, will be better understood when read in conjunction with the appended drawings.

FIG. 1, comprising

FIG. 2, comprising

FIG. 3 is a graph depicting the results of quantitative beta-galactosidase enzymography of arterial smooth muscle cells grown on native collagen and denatured collagen after transfection following lipofection using beta-galactosidase plasmid DNA and Lipofectamine®.

FIG. 4, comprising

FIG. 6, comprising

Figure 6A:
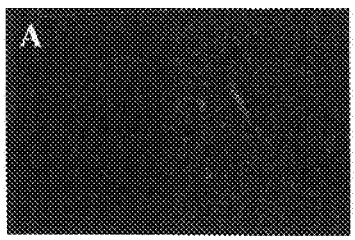
FIGS. 6A, 6B and 6C, is a series of images depicting the fluorescence of A10 cells grown on native type I collagen after transfection with p-EGFP-N3
Figure 6B:
Figure 6C:
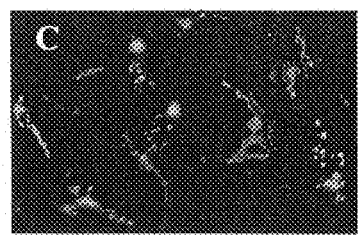

(green fluorescent protein) plasmid DNA. Immediately after transfection, the cells were either not provided cytochalasin D (FIG. 6A), provided cytochalasin D for thirty minutes (FIG. 6B), or incubated with cytochalasin D overnight (FIG. 6C).

Figure 7A:
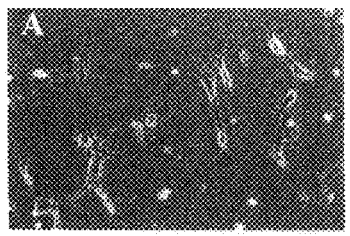
Figure 7B:
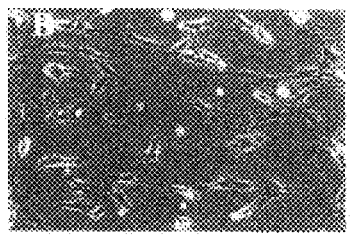
Figure 7C:
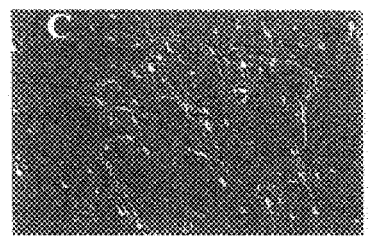

FIG. 7, comprising FIGS. 7A, 7B and 7C, is a series of images depicting bright field micrographs of A10 cells grown on native type I collagen after transfection with p-EGFP-N3 (green fluorescent protein) plasmid DNA. Immediately after transfection, the cells were either not provided cytochalasin D (FIG. 7A), provided cytochalasin D for thirty minutes (FIG. 7B) or incubated with cytochalasin D overnight (FIG. 7C).

DETAILED DESCRIPTION OF THE INVENTION

The present invention relates to methods and compositions for enhancing the efficiency of delivery of a nucleic acid to a cell. The inventive methods comprise the use of an agent capable of enhancing the cytoskeletal permissiveness of the cell for transfection along with a nucleic acid delivery system to enhance the delivery of a nucleic acid to a cell to be transfected. The cytoskeletal permissiveness of the cell for transfection can be enhanced, by way of example and not by limitation, by reducing the overall electronegative charge of the milieu surrounding or the cytoplasm of a cell to be transfected, by inhibiting the activity of a nuclease in the milieu surrounding or the cytoplasm of a cell to be transfected, or by enhancing the level of G-Actin in the cell to be transfected. By providing a means of enhancing the efficiency of delivery of a nucleic acid to a cell, the methods and compositions of the present invention are of great value in overcoming barriers to successful therapeutic and prophylactic applications of gene therapy in mammals.

The present invention is useful for enhancing the efficiency of delivery of a nucleic acid to virtually any type of cell which could be a therapeutic target in gene therapy strategies or a desired target for transfection with a nucleic acid. The inventive methods and compositions thus provide great advantages for virtually all gene therapy strategies. The inventive methods and compositions are particularly useful for enhancing the efficiency of delivery of plasmid DNA to mammalian cells or enhancing the efficiency of adeno-associated virus and retrovirus vector delivery of a nucleic acid to mammalian cells, since these strategies presently result in poor levels of transgene expression. The invention is also useful for enhancing the efficiency of tissue-specific in situ delivery of a nucleic acid to specific cells to be transfected. As such, the therapeutic protein to be expressed after transfection can be disease or tissue-specific.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, "enhancing the efficiency of delivery of a nucleic acid to a cell" means to increase the amount of or to sustain the presence of a nucleic acid in a cell into which the nucleic acid is transfected. This enhancement can be brought about by any one or more of several means, including, by way of example and not by limitation, initiating, maintaining and prolonging episomal or integrated nucleic acid expression, and by facilitating the proper trafficking of a nucleic acid vector to the nucleus of a cell in which it is expressed.

As used herein, "enhancing the cytoskeletal permissiveness of a cell for transfection" means to reduce either directly or indirectly any one or more of the biochemical and physiological barriers presented by the cytoskeleton to the transfection of a cell with a nucleic acid. Such barriers include, by way of example and not by limitation, the overall electronegative charge of the milieu surrounding or the cytoplasm of the cell to be transfected and the activity of nucleases in the milieu surrounding or the cytoplasm of the cell to be transfected.

As used herein, a "nucleic acid delivery system" means any composition or system, known or to be known in the art, which can be used to deliver a nucleic acid into a cell. Such systems include any composition for delivery of a nucleic acid into a cell which permits retention of the structure and function of the nucleic acid. By way of example, and not by limitation, such systems include the following: "naked" (i.e. non-complexed) nucleic acids; nucleic acids complexed with cationic molecules such as polylysine and liposome-forming lipids; vectors such as a plasmid vector, a viral vector, an antisense oligonucleotide, an adenovirus, an adeno-associated virus, a retrovirus, a lentivirus, a herpesvirus, and a bacteriophage; and a linearized nucleic acid.

As used herein, the term "vector" means a composition of matter which comprises an isolated nucleic acid and which can be used to deliver the isolated nucleic acid to the interior of a cell.

As used herein, the term "expression vector" means a vector comprising a recombinant polynucleotide comprising expression control sequences operatively linked to a nucleotide sequence to be expressed. The vectors described herein specifically include expression vectors. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, the term "nucleic acid" means any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

As, used herein, by describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, the term "promoter" means a nucleic acid sequence which is required for expression of a gene product operably linked to the promoter. In some instances, this sequence may be the core promoter sequence and in other instances, this sequence may also include an enhancer sequence and other regulatory elements which are required for expression of the gene product. The promoter may, for example, be a constitutive or an inducible promoter.

A "constitutive" promoter is a nucleotide sequence which, when operably linked with a polynucleotide which encodes or specifies a gene product, causes the gene product to be produced in a living human cell without requiring an inducer.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

As used herein, the term "pharmaceutically-acceptable carrier" means a chemical composition with which at least one of an agent, a nucleic acid delivery system and any component thereof may be combined, and which, following the combination, can be used to administer the appropriate agent, nucleic acid delivery system or component thereof to a mammal.

Description

The present invention includes a method of enhancing the efficiency of delivery of a nucleic acid to a cell to be transfected with the nucleic acid. The inventive method comprises providing to a cell an agent capable of enhancing the cytoskeletal permissiveness of the cell for transfection in an amount effective to enhance the cytoskeletal permissiveness. The method also includes providing to the cell a nucleic acid delivery system for the transfection of the cell with a desired nucleic acid. The inventive method provides an enhancement in the efficiency of delivery of a nucleic acid to the cell being transfected.

The cell is preferably within a tissue in a mammal, and while it can be any type of cell, it is therefore preferably a mammalian cell and more preferably a human cell. The human cell is preferably a cell which is bound to an extracellular matrix (i.e. not a circulating cell), although a progenitor of a circulating cell is also preferred. Examples of such preferred cells include diseased or normal cells of a diseased tissue or organ, all types of tumor cells, all types of progenitor cells including all types of stem cells, cells to be transfected for vaccination purposes (i.e. using a DNA vaccine) and cell lines grown in culture.

The nucleic acid to be delivered can be any type of nucleic acid, either naturally occurring or synthetic. It is not intended that the present invention be limited by the nature of the nucleic acid employed. The nucleic acid may be from a viral, bacterial, animal or plant source. The nucleic acid may be DNA or RNA and may exist in a double-stranded, single-stranded or partially double-stranded form. Furthermore, the nucleic acid may be found as part of a virus or other macromolecule (See, e.g., Fasbender et al., 1996, J. Biol. Chem. 272:6479–89 describing polylysine condensation of DNA in the form of adenovirus).

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g. Gait, 1985, *Oligonucleotide Synthesis: A Practical Approach* (IRL Press, Oxford, England)). RNAs may be produce in high yield via in vitro transcription using plasmids such as SP65 (Promega Corporation, Madison, Wis.).

In some circumstances, for example, where increased nuclease stability is desired, nucleic acids having modified internucleoside linkages may be preferred. Nucleic acids containing modified internucleoside linkages may also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2-$), diinethylene-sulfoxide ($-CH_2-SO-CH_2-$), dimethylene-sulfone ($-CH_2-SO_2-CH_2-$), 2'-O-alkyl, and 2'-deoxy-2'-fluoro phosphorothioate internucleoside linkages are well known in the art (see Uhlmann et al., 1990, *Chem. Rev.* 90:543–584; Schneider et al., 1990, *Tetrahedron Lett.* 31:335 and references cited therein).

The nucleic acids may be purified by any suitable means well known in the art. For example, the nucleic acids can be purified by reverse phase or ion exchange HPLC, size exclusion chromatography or gel electrophoresis. Of course, the skilled artisan will recognize that the method of purification will depend in part on the size of the DNA to be purified.

Nucleic acids comprising either a naturally-occurring or a modified gene sequence (i.e. genes having sequences that differ from the gene sequences encoding the naturally-occurring proteins) are encompassed by the invention. These modified gene sequences include modifications caused by point mutations, modifications due to the degeneracy of the genetic code or naturally occurring allelic variants, and further modifications that have been introduced by genetic engineering, i.e., by the hand of man.

Techniques for introducing changes in nucleotide sequences that are designed to alter the functional properties of the encoded proteins or polypeptides are well known in the art. Such modifications include the deletion, insertion, or substitution of bases, and thus, changes in the amino acid sequence. Changes may be made to increase the activity of a protein, to increase its biological stability or half-life, to change its glycosylation pattern, and the like. All such modifications to the nucleotide sequences encoding such proteins are encompassed by this invention.

In the inventive method, the agent capable of enhancing the cytoskeletal permissiveness of the cell for transfection can be any compound, including by way of example and not by limitation, a drug, a pharmaceutical composition, a nucleic acid, an oligonucleotide, a gene, a protein, a polypeptide and a peptide, among others.

The agent can be obtained from any natural or synthetic source. For example, where the agent is a naturally occurring protein or nucleic acid, the agent can be prepared by any one or more of the following methods. The agent can be isolated from a biological material (e.g., a biological fluid or tissue sample) using any method of isolating or purifying a protein or nucleic acid from a biological material known to the skilled artisan. Such methods are described, for example, in Deutscher et al. (ed., 1990, *Guide to Protein Purification* Harcourt Brace Jovanovich, San Diego).

Alternatively, the agent can be obtained by preparing a recombinant version thereof (i.e., by using the techniques of genetic engineering to produce a recombinant protein or a recombinant nucleic acid which can then be isolated or purified as described above). Furthermore, such an agent can be obtained synthetically, for example, by chemically synthesizing a protein or a nucleic acid by any method of synthesis known to the skilled artisan. The synthesized agent can then be purified by any method known in the art.

In one preferred embodiment of the inventive method, the agent is denatured collagen or a peptide thereof. The collagen may be any type of collagen. Preferably, the collagen is a type which can be a substrate for a matrix metalloproteinase (MMP), and more preferably, a substrate for MMP-2. An example of a preferred collagen is type I collagen. The peptide thereof can be any peptide of sufficient size to be acted upon by a MMP hydrolytic binding site.

In another preferred embodiment, the agent is an actin binding protein or a peptide thereof. The Thymosins are a family of actin binding proteins which have previously been described (See, for example, Low et al., 1981, Proc. Nat. Acad. Sci., USA, 78(2):1162–1166; Safer et al., 1990, Proc. Nat. Acad. Sci., USA 78:2536–2540; Low et al., 1985, Methods Enzymol. 116:248–255; and Nachmias, 1993, Curr. Opin. Cell Biol. 5:56–62). A preferred actin binding protein is Thymosin beta-4 (TB4) or a peptide thereof. TB4 is the most abundant intracellular actin binding protein of mammals. TB4 is an actin binding protein which was has been implicated in cellular functions such as maintaining a pool of G-Actin, wound healing, migration and angiogenesis. The structure and cellular function of TB4 has been reviewed, for example, in Low et al., 1985, Methods in Enzymol. 116:248–255 and Nachmias, 1993, Curr. Opin. Cell Biol. 5:56–62.

In another preferred embodiment, the agent is Tenascin C or a peptide thereof. Tenascin C is a protein which is described herein in the inventive compositions. In one aspect, the agent comprises both Tenascin C and TB4.

In one preferred aspect, the agent in the inventive methods is an agent selected from the group consisting of Tenascin C or a peptide thereof, an actin-binding protein such as TB4 or a peptide thereof, an actin depolymerization agent, a cytochalasin, a modulator of TB4, a modulator of an intermediate in the Tenascin C and TB4 receptor-signaling pathway, a nuclease inhibitor, and denatured collagen or a peptide thereof. The cytochalasins are a series of mold metabolites known to affect actin polymerization and microtubule assembly in eukaryotic cells. They are heterofunctional bio-organic compounds having molecular weights in the 500 dalton range, and are generally soluble in dimethylsulfoxide and related solvents. The use of cytochalasins has been described, for example in Bradke et al., 1999, Science 283:1931–1934 and Cooper, 1987, J. Cell Biol. 105:1473–1478.

In one embodiment, the agent is an isolated nucleic acid encoding a protein or a polypeptide which, when expressed in a cell to be transfected, is capable of enhancing the cytoskeletal permissiveness of the cell for transfection. Preferably, the isolated nucleic acid encodes one or more of Tenascin C, TB4 and peptides thereof.

The agent can be provided to the cell either alone in "naked" form, for example, as a "naked" nucleic acid or a purified protein, or formulated in a vehicle suitable for delivery, such as, by way of example and not limitation, in a complex with a cationic molecule or a liposome forming lipid, or as a component of a vector, or a component of a pharmaceutical composition. Such vehicles are known in the art and are discussed herein.

The agent can be provided to the cell either directly, such as by contacting the agent with the cell, or indirectly, such as through the action of any biological process. Virtually any method of attaining entry of the agent into the cell can be used, including, by way of example and not by limitation, endocytosis, receptor targeting, coupling with native or synthetic cell membrane fragments, physical means such as electroporation, combining the agent with a polymeric carrier such as a controlled release film or nanoparticle or microparticle, using a vector, injecting the agent into a tissue or fluid surrounding the cell, simple diffusion of the agent across the cell membrane, or by any active or passive transport mechanism across the cell membrane.

The agent is provided to the cell in an amount effective to enhance the cytoskeletal permissiveness of the cell for transfection. The effective amount is an amount of the agent which, when provided to a cell, results in increased cytoskeletal permissiveness of the cell for transfection, relative to an otherwise identical cell which is not provided the effective amount of the agent. For example, the effective amount can range from about 1 picogram to about 100 milligrams of the agent.

The nucleic acid delivery system comprising the desired nucleic acid can be provided to the cell simultaneously with providing the agent for enhancing cytoskeletal permissiveness, or it may be provided prior to or after providing the agent.

The nucleic acid delivery system can be any of the nucleic acid delivery systems described herein, or others known or to be known in the art. Various nucleic acid delivery systems are described, for example in Sambrook et al., 1989, *Molecular Cloning: A Laboratory Manual*, Cold Spring Harbor Laboratory, New York; and Ausubel et al., 1994, *Current Protocols in Molecular Biology*, John Wiley & Sons, New York. Such nucleic acid delivery systems comprise the desired nucleic acid, by way of example and not by limitation, in either "naked" form as a "naked" nucleic acid, or formulated in a vehicle suitable for delivery, such as in a complex with a cationic molecule or a liposome forming lipid, or as a component of a vector, or a component of a pharmaceutical composition.

The nucleic acid delivery system can be provided to the cell either directly, such as by contacting it with the cell, or indirectly, such as through the action of any biological process. By way of example, and not by limitation, the nucleic acid delivery system can be provided to the cell by endocytosis, receptor targeting, coupling with native or synthetic cell membrane fragments, physical means such as electroporation, combining the nucleic acid delivery system with a polymeric carrier such as a controlled release film or nanoparticle or microparticle, using a vector, injecting the nucleic acid delivery system into a tissue or fluid surrounding the cell, simple diffusion of the nucleic acid delivery system across the cell membrane, or by any active or passive transport mechanism across the cell membrane. Additionally, the nucleic acid delivery system can be provided to the cell using techniques such as antibody-related targeting and antibody-mediated immobilization of a viral vector.

Where a vector is used as the vehicle for providing one or more of the nucleic acid delivery system or the agent, the vector can be any type of vector known to the skilled artisan. Preferably, the vector is either a plasmid vector, a viral vector or a linearized nucleic acid. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

In one embodiment of the inventive method, the nucleic acid delivery system is provided to the cell simultaneously with providing the agent. In this embodiment, the agent can be either coincorporated with the nucleic acid delivery system, or it can be provided simultaneously in a different vehicle. Suitable vehicles for providing the agent are discussed above. Alternatively, the agent can be provided to the cell without using a vehicle simultaneously with providing the nucleic acid delivery system. Suitable methods for providing the agent without using a vehicle are discussed herein.

In another embodiment, the nucleic acid delivery system is provided to the cell prior to providing the cell with the agent.

In a further embodiment, the nucleic acid delivery system is provided to the cell after providing the cell with the agent.

Preferably, the agent and/or nucleic acid delivery system are provided (e.g. administered) in a manner which enables tissue-specific uptake of the agent and/or nucleic acid delivery system. Preferred techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

In one aspect of the invention, at least one of the agent and the nucleic acid delivery system is provided to the cell formulated as a pharmaceutical composition. The agent and the nucleic acid delivery system can either be formulated together in the same pharmaceutical composition or separately in different pharmaceutical compositions. Also, the components of the agent can either be formulated together in the same pharmaceutical composition or separately in different pharmaceutical compositions. Similarly, the components of the nucleic acid delivery system can either be formulated together in the same pharmaceutical composition or separately in different pharmaceutical compositions. The pharmaceutical composition comprises a pharmaceutically-acceptable carrier and at least one of an agent capable of enhancing the cytoskeletal permissiveness of the cell for transfection in an amount effective to enhance the cytoskeletal permissiveness, a nucleic acid delivery system, and any component thereof.

The pharmaceutical compositions useful for practicing the invention may be administered to deliver to a desired cell a dose of between 0.1 nanograms per kilogram per day and 100 milligrams per kilogram per day of the agent and/or the nucleic acid delivery system. In one embodiment, the invention envisions administration to a mammal of a dose which results in a concentration of the appropriate agent and/or nucleic acid delivery system between 0.1 micromolar and 100 micromolar in a tissue of a mammal containing a cell sought to be transfected.

Pharmaceutical compositions that are useful in the methods of the invention may be administered by any route of administration to a mammal for a pharmaceutical composition known to the skilled artisan. By way of example and not by limitation, the pharmaceutical composition can be administered to a mammal systemically in an oral formulation, parenterally by injection, topically by administration directly to a specific tissue containing a cell to be transfected, or by using a technique for in situ delivery to a specific target tissue, such as by using iontophoresis and activation through an external energy source such as a magnetic field, ultrasound energy or nuclear energy.

In addition to the pharmaceutically-acceptable carrier and the agent and/or the nucleic acid delivery system or component thereof, such pharmaceutical compositions may contain other ingredients known to enhance and facilitate drug administration. Other possible formulations, such as nanoparticles, liposomes, resealed erythrocytes, and immunologically based systems may also be used to administer an appropriate agent and/or nucleic acid delivery system according to the methods of the invention.

In one embodiment of the method of the invention, enhancing the cytoskeletal permissiveness of the cell for transfection comprises inhibiting DNAase I activity in the milieu surrounding or the cytoplasm of the cell to be transfected. DNAase I activity can be inhibited by any method known in the art for inhibiting the activity of a nuclease.

Preferably, DNAase I activity is inhibited by enhancing the level of G-Actin in the cell.

In another aspect, the DNAase I activity is inhibited by transfecting the cell to result in the overexpression of the DNAase I binding region of G-Actin. In this embodiment, the agent capable of enhancing the cytoskeletal permissiveness of the cell for transfection is an isolated nucleic acid comprising the gene encoding the DNAase I binding region of G-Actin, and is provided to the cell as a component of a vector such as an adenovirus vector or a plasmid vector. The gene encoding the DNAase I binding region of the actin gene can readily be identified and cloned using standard techniques known in the art. For example, the DNAase I binding region can be isolated using synthetic peptide mapping or deletion mapping of the G-Actin protein. In peptide mapping, a series of synthetic peptides are prepared and tested in vitro for binding with DNAase I in competition with G-Actin. Specific peptides which compete with G-Actin for binding are identified and, tested for inhibition of DNAase I activity in a cell. The DNA fragment encoding the identified peptide is then cloned into an expression vector for the transfection and overexpression of the peptide in a targeted cell.

The overexpression of the DNAase I binding region of G-Actin inhibits the DNAase I activity by competitive inhibition. The overexpressed DNAase I binding region of G-Actin binds with DNAase I present in the cell, thus inhibiting degradation by DNAase I of the nucleic acid sought to be transfected into the cell. This competitive inhibition inhibits DNAase I activity and thus the degradation of the nucleic acid sought to be transfected in the cell.

In addition to the methods described above, the DNAase I binding region of G-actin can be obtained by any of the methods discussed herein for obtaining an agent capable of enhancing the cytoskeletal permissiveness of the cell for transfection. In one aspect, the DNAase I binding region of G-actin is administered to a cell as an agent in the form of a purified or recombinant polypeptide.

In another embodiment of the inventive method, enhancing the cytoskeletal permissiveness of the cell for transfection comprises reducing the overall electronegative charge of the milieu surrounding or the cytoplasm of the cell to be transfected.

Preferably, reducing the overall electronegative charge of the milieu surrounding or the cytoplasm of the cell to be transfected comprises enhancing the level of G-Actin in the cell. The level of G-Actin in the cell can be enhanced by any method known to the skilled artisan. An enhancement in the level of G-Actin in a cell can be assessed by any method known in the art for assessing relative levels of a protein in a cell. Such methods include, for example, the use of gel electrophoresis, HPLC methods, and specific binding assays. For example, an assay is commercially available (Cytoskeleton Inc., Denver, Colo.) which detects the amount of binding of G-Actin to DNAase I (See, Blikstad et al., 1978, Cell 15:932–943).

In one aspect, the level of G-Actin in the cell is enhanced by enhancing the transition from F-Actin to G-Actin. Any method known to the skilled artisan for enhancing this transition can be used. In one embodiment, enhancing the level of G-Actin in the cell comprises depolymerizing F-Actin to G-Actin. In one aspect, an actin binding protein is used to depolymerize F-Actin to G-Actin. The use of actin binding proteins is known in the art to effect depolymerization of F-Actin to G-Actin. A preferred actin binding protein in this embodiment is TB4. Actin binding proteins (including TB4, profilin, gelsolin, vilin, actin depolymerizing factor {ADF} and cofilin) and their roles in the depolymerization of F-Actin to G-Actin have been well studied and are described, for example, in Sohn et al., 1994, BioEssays 16: 465–472; Safer et al., 1994, BioEssays 16: 473–479; Matsudaira et al., 1988, Cell 54: 139–140; and Hawkins et al., 1993, Biochemistry 32:9985–9993.

In another aspect, the depolymerization of F-Actin to G-Actin is effected by manipulating the ion channel-based control of actin polymerization. For example, the agent capable of enhancing the cytoskeletal permissiveness of the cell can be a compound which is effective at modulating an ion channel in the cell. Contractile protein assembly is known in the art to be stimulated by electrical-mechanical events via action potentials within the cell. Thus, by way of example, ion channel blockade using a compound which is effective as an ion channel blocker can be used to interfere with actin polymerization, thereby enhancing the level of G-Actin in the cell.

In another embodiment, the inventive method comprises enhancing the level of G-Actin in the cell, wherein the agent is a compound capable of rendering G-Actin less susceptible to proteolysis upon binding with G-Actin. The compound can be any compound, such as a drug, a salt of a metal, a peptide or a protein, which, upon binding with G-Actin, renders G-Actin less susceptible to proteolytic degradation than an otherwise identical molecule of G-Actin which is not bound to the compound. Preferred compounds include beryllium fluoride (See, e.g. J. Biol. Chem., 269:11852–11858) and cadmium salts (See, e.g. 1996, Tox. Appl. Pharm. 139:115–121).

In another embodiment of the inventive method, enhancing the level of G-Actin in the cell comprises upregulating the expression of TB4 either directly or indirectly. Directly upregulating the expression of TB4 means to enhance the expression of TB4 by acting directly upon the promoter which drives expression of a gene encoding TB4. For example, the expression of TB4 can be upregulated directly by providing to the cell, as the agent capable of enhancing the cytoskeletal permissiveness of the cell for transfection, an isolated nucleic acid encoding TB4 as a component of a vector for the over-expression of TB4 in the cell to be transfected. The vector can be any type of vector described herein or known to the skilled artisan. A vector which is designed to enhance expression of TB4 comprises either an inducible promoter, or a constitutive promoter, wherein either promoter drives high level expression of the gene to which it is operably linked. A non-limiting example of a constitutive promoter which is useful in this context is the cytomegalovirus immediate early promoter. A non-limiting example of an inducible promoter is the tetracycline promoter, which upon addition of tetracycline to a cell containing this promoter, induces high levels of expression of the gene to which the promoter is operably linked. These and other promoters are well known in the art and are described, for example, in Sambrook et al., 1989, *Molecular Cloning: A Laboratory Manual*, Cold Spring Harbor Laboratory, New York; Ausubel et al., 1994, *Current Protocols in Molecular Biology*, John Wiley & Sons, New York; and Gerhardt et al., eds., 1994, *Methods for General and Molecular Bacteriology*, American Society for Microbiology, Washington, DC.

In one aspect, the agent is selected from the group consisting of a TB4 promoter, a molecule which participates in cell—cell interactions, a molecule involved in cell—cell adhesion, and a synthetic extracellular matrix molecule construct having design features effective to enhance the cytoskeletal permissiveness of a cell for transfection. The agent can incorporate one or more design features for enhancing the efficiency of delivery of a nucleic acid to a cell by enhancing the cytoskeletal permissiveness of the cell for transfection. Such design features can involve, by way of example and not by limitation, the following: a) the control of actin status (i.e. controlling the state of actin polymerization to favor the depolymerized state, that is, G-Actin as the preferred state over F-Actin); b) the use of any of the actin binding proteins described herein, which facilitate the F-Actin to G-Actin transition; c) controlling the expression of one or more actin binding proteins; d) using one or more exogenous recombinant actin binding proteins or peptides thereof; e) using one or more exogenous actin manipulating agents which are capable of depolymerizing F-Actin to G-Actin, such as cytochalasin D; and f) exerting extracellular matrix control by using one or more extracellular matrix proteins such as Tenascin C, which signals through RGD receptors to upregulate actin binding proteins such as TB4.

The expression of TB4 can be upregulated indirectly by providing to the cell a Tenascin C inducing substrate as the agent capable of enhancing the cytoskeletal permissiveness of the cell for transfection. A Tenascin C inducing substrate is any substance which is capable of inducing the expression and extracellular deposition of Tenascin C. Indirectly upregulating TB4 means to increase the expression of TB4 through an increase in the expression of an intermediate (i.e. Tenascin C) which in turn acts upon the promoter which drives expression of a gene encoding TB4. The upregulation of Tenascin C results in upregulation of the expression of TB4. While not wishing to be bound by any particular theory, it is suspected that Tenascin C upregulates TB4 through an interaction with an appropriate receptor (specific integrin), intracellular signaling involving specific protein kinase activity, activation of the TB4 promoter through transcriptional factors, and post-translational assembly. Tenascin C is a protein which is abundantly expressed within remodeling tissues, including blood vessels, wounds and tumors. Tenascin C regulates cellular migration and proliferation-associated events, alters vascular smooth muscle shape, and amplifies the proliferative response of vascular smooth muscle cells by promoting growth factor receptor clustering and phosphorylation.

Preferably, the Tenascin C inducing substrate is denatured collagen, a peptide thereof or a Tenascin C receptor. Providing to the cell a Tenascin C inducing substrate results in the upregulation of Tenascin C through the action of the Tenascin C promoter.

Preferably, the cell is provided a Tenascin C inducing substrate by growing the cell on a medium containing denatured collagen or a peptide thereof.

Figure 5:
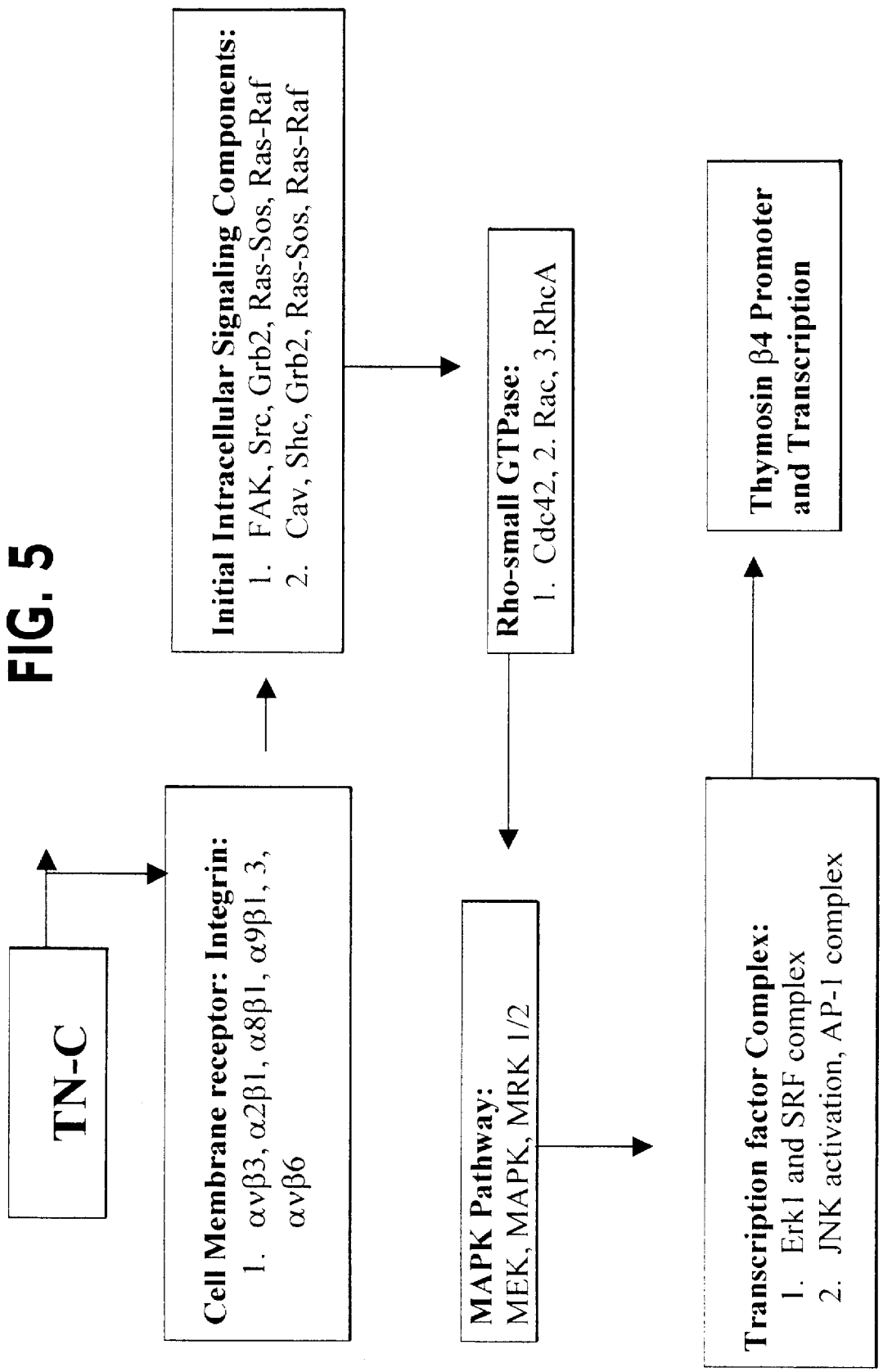
FIG. 5 is a schematic illustrating various intermediates in the receptor-signaling pathway of Tenascin C (TN-C) and Thymosin beta-4.

In another embodiment of the inventive method, enhancing the level of G-Actin in the cell comprises upregulating the expression of TB4 indirectly by providing to the cell, as the agent capable of enhancing the cytoskeletal permissiveness of the cell for transfection, a modulator of an intermediate in the Tenascin C and TB4 receptor-signaling pathway. The modulator can be any compound, and can be, by way of example and not by limitation, a drug, a peptide or a protein. The intermediates in the Tenascin C and TB4 receptor-signaling pathway are depicted in FIG. 5, and include cell membrane receptors (integrins), initial signaling elements (oncogene products, e.g. Src and Ras), GTPase activity for G-protein related signaling, mitogen associated kinase activation (MAPK pathway), transcriptional control (Erk1, etc.) and upregulation of the TB4 promoter.

Preferably, the modulator is effective at enhancing signal-transduction within the cell for increasing TB4 expression. Examples of preferred modulators include factors which regulate MMPs, such as tyrosine phosphorylated proteins, egr-1 and AP-1.

The invention also includes a composition for enhancing the efficiency of delivery of a nucleic acid to a cell. The inventive composition is useful in the methods of the invention discussed above for enhancing the efficiency of delivery of a nucleic acid to a cell. The inventive composition comprises an agent capable of enhancing the cytoskeletal permissiveness of a cell for transfection in an amount effective to enhance the permissiveness of the cell for transfection. Additionally, the inventive composition comprises a nucleic acid delivery system for the transfection of the cell. The components of the composition of the invention are the same as those described above in the inventive methods.

The nucleic acid can be any type of nucleic acid described herein. The cell can be any type of cell, and is preferably a mammalian cell, and more preferably a human cell of the types described herein in the inventive methods. The agent can be any of the agents for enhancing the cytoskeletal permissiveness of the cell for transfection described herein in the inventive methods.

In one preferred aspect, the agent in the inventive compositions is an agent selected from the group consisting of Tenascin C or a peptide thereof, an actin-binding protein such as TB4 or a peptide thereof, an actin depolymerization agent, a cytochalasin, a modulator of TB4, a modulator of an intermediate in the Tenascin C and TB4 receptor-signaling pathway, a nuclease inhibitor, and denatured collagen or a peptide thereof. The cytochalasins are a series of mold metabolites known to affect actin polymerization and microtubule assembly in eukaryotic cells. They are heterofunctional bio-organic compounds having molecular weights in the 500 Dalton range, and are generally soluble in dimethylsulfoxide and related solvents. The use of cytochalasins has been described, for example in Bradke et al, 1999, Science 283:1931–1934 and Cooper, 1987, J. Cell Biol. 105:1473–1478.

In another preferred embodiment, the agent is an isolated nucleic acid encoding a protein or polypeptide which, when expressed in a cell, is capable of enhancing the cytoskeletal permissiveness of the cell for transfection. Preferably, the protein or polypeptide encoded by the isolated nucleic acid is one or more of TB4, Tenascin C and peptides thereof.

In one aspect, the amount of the agent in the inventive composition ranges from about 1 picogram to about 100 milligrams. For example, when the agent is recombinant Tenascin C, the Tenascin C is present in the composition in an amount which results in a local concentration in a targeted cell from about 1 to about 50 micrograms per milliliter. Also by way of example, where the agent is recombinant TB4, the TB4 is present in the composition in an amount which results in a local concentration in a targeted cell from about 0.1 to about 100 micrograms per milliliter.

The nucleic acid delivery system can be any of the nucleic acid delivery systems described herein in the inventive methods. Preferably, the nucleic acid delivery system is a plasmid vector, a viral vector or a linearized nucleic acid.

Where the composition of the invention comprises as the agent an isolated nucleic acid encoding a protein or polypeptide capable of enhancing the cytoskeletal permissiveness of the cell for transfection, the isolated nucleic acid can be either a component of the same nucleic acid delivery system used to transfect the cell, or a component of a separate nucleic acid delivery system. For example, the isolated nucleic acid can be a gene or a portion of a gene which is incorporated into a plasmid vector which is used as the same nucleic acid delivery system to deliver the nucleic acid with which the cell is to be transfected. In this embodiment, the plasmid vector has multiple expression regions with separate regulatable promoters (for example, a region encoding Tenascin C or TB4 {i.e. the isolated nucleic acid} or a peptide thereof, plus a region encoding a functional protein of interest). Thus, the construct comprises a "functional" region comprising the functional gene of interest, and an "enhancing" region, comprising an isolated nucleic acid encoding the protein or polypeptide which, when expressed in the cell to be transfected, is capable of enhancing the cytoskeletal permissiveness of the cell for transfection. Similar constructs can be designed using the viral vectors and any of the other nucleic acid delivery systems described herein.

The invention also includes a kit for enhancing the efficiency of delivery of a nucleic acid to a cell. The kit comprises an instructional material describing the use of the kit in an inventive method of enhancing the efficiency of delivery of a nucleic acid to a cell. As used herein, an "instructional material" includes a publication, a recording, a diagram, or any other medium of expression which can be used to communicate the usefulness of the inventive method or composition for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The kit also comprises an agent capable of enhancing the cytoskeletal permissiveness of a cell for transfection. The agent can be any of the agents described herein, and is present in an amount effective to enhance the cytoskeletal permissiveness of the cell for transfection. Preferably, the agent is selected from the group consisting of denatured collagen or a peptide thereof, Tenascin C or a peptide thereof and an isolated nucleic acid encoding therefor, and TB4 or a peptide thereof and an isolated nucleic acid encoding therefor.

The kit also comprises a nucleic acid delivery system. The nucleic acid delivery system can be any of the nucleic acid delivery systems described herein.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLE 1

The objective of the experiments described in this example was to ascertain whether denatured collagen, which is able to provoke a marked change in cell shape to a shape hypothesized to enhance the cytoskeletal permissiveness of a cell for transfection with a nucleic acid, would be effective at enhancing the extent of transfection of cells. The results of these experiments indicated that denatured collagen was effective at enhancing the efficiency of delivery of a nucleic acid to a cell, thus increasing the extent of transfection observed in the cells.

Figure 1A:
FIGS. 1A and 1B, is a pair of images depicting A10 cells grown on native collagen and denatured collagen, respectively, forty-eight hours after transfection using plasmid nuclear targeted beta-galactosidase.
Figure 1B:
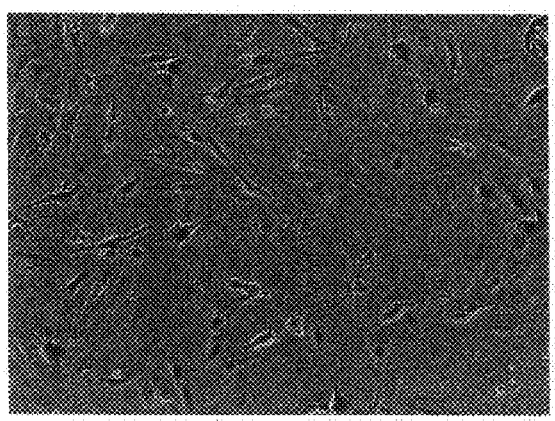
Figure 2A:
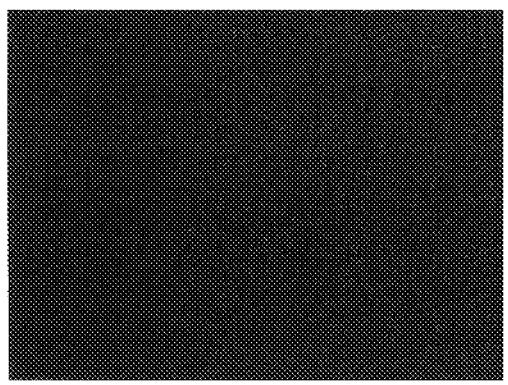
FIGS. 2A and 2B, is a pair of images depicting the fluorescence of A10 cells grown on native collagen and denatured collagen, respectively, twenty-four hours after transfection with p-EGFP-N3 (green fluorescent protein) plasmid DNA.
Figure 2B:

Rat arterial smooth muscle cells (A10 cells) grown on denatured collagen and native fibrillar type I collagen were studied. A change in cell shape from stellate to elongated with reorientation of the actin-stress fibers was observed. When these cells were transfected with a nuclear targeted beta-galactosidase plasmid (CMV promoter) complexed with cationic lipid (Lipofectamine®), greater than 20% of the cells (FIGS. 1 and 2) grown on the denatured collagen (in a formulation hypothesized to lead to TB4 being upregulated) were successfully transfected, whereas the cells grown on native collagen exhibited almost no transfection. Quantitative beta-galactosidase enzymography (FIG. 3) confirmed these results, as did transfection with GFP (green fluorescent protein) DNA.

In a related experiment, circumstances were created which promoted a cytoskeletal change to one with increased intracellular TB4 and thus increased G-Actin. Rat arterial smooth muscle cells (A10 cells) were grown on either native collagen or denatured type I bovine collagen (gelled at pH 7.4, 37° C.) and then compared to those cells grown on denatured type I bovine collagen (denatured at 100° C. for one hour at pH 3.0), and dried as a film on culture plates. The cells which were grown on native collagen exhibited a stellate configuration, and demonstrated little or no transfection following lipofection using beta-galactosidase plasmid DNA and Lipofectamine®. In contrast, the cells that were grown on denatured collagen (using the same cell number for both cases) exhibited an elongated morphology, and demonstrated more than 20% of cells transfected. Quantitative enzyme assays confirmed the enhancement of expression (FIG. 3). An independent GFP experiment (FIG. 2) using A10 cells confirmed this result.

EXAMPLE 2

The objective of the experiment described in this Example was to ascertain whether Tenascin C itself was able to enhance the cytoskeletal permissiveness of a cell for transfection with a nucleic acid, thereby resulting in an increase in the extent of transfection of cells grown on native collagen containing Tenascin C relative to cells grown on native collagen alone. The results of these experiments indicated that Tenascin C itself was effective at enhancing the efficiency of delivery of a nucleic acid to a cell, thus increasing the extent of transfection.

A10 cells were grown on native type I collagen containing 0, 15 and 50 micrograms per milliliter of Tenascin C. The cells were transfected with p-EGFP-N3 (green fluorescent protein) plasmid DNA. Twenty-four hours after transfection, the fluorescence of cells grown on the native type I collagen containing 0, 15 and 50 micrograms per milliliter of Tenascin C (FIGS. 4A, 4B and 4C, respectively) was assessed. A bright field micrograph (FIG. 4D) was also taken of the cells grown on native type I collagen containing 15 micrograms per milliliter of Tenascin C. As shown in FIGS. 4A, 4B, 4C and 4D, providing Tenascin C to the cells grown on native type I collagen resulted in a dose-dependent increase in transfection of A10 cells, as evidenced by the dose-dependent increase in GFP expression.

Figure 4A:
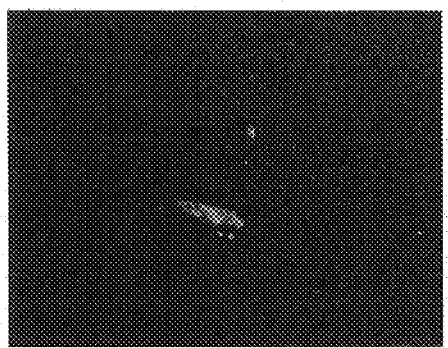
FIGS. 4A, 4B, 4C and 4D, is a series of images depicting the fluorescence of A10 cells grown on native type I collagen containing 0, 15 and 50 micrograms per milliliter of Tenascin C (FIGS. 4A, 4B and 4C, respectively) twenty-four hours after transfection with p-EGFP-N3 (green fluorescent protein) plasmid DNA, and an image of a bright field micrograph (FIG. 4D) depicting A10 cells grown on native type I collagen containing 15 micrograms per milliliter of Tenascin C.
Figure 4B:
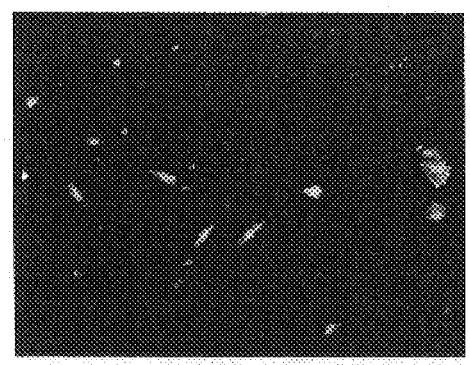
Figure 4C:
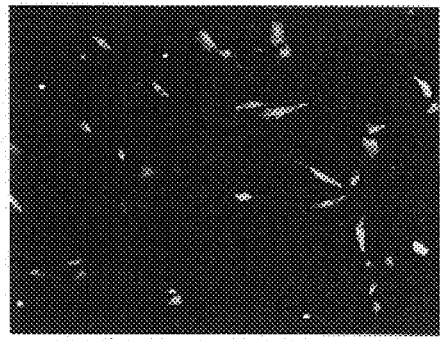
Figure 4D:
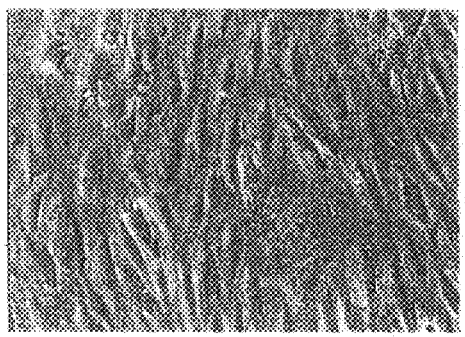

The cells grown on native type I collagen in the absence of Tenascin C exhibited almost no transfection (FIG. 4A). In contrast, cells grown on native type I collagen containing 15 micrograms per milliliter of Tenascin C exhibited increased transfection (FIG. 4B), and cells grown on native type I collagen containing 50 micrograms per milliliter of Tenascin C exhibited the highest degree of transfection (FIG. 4C). The bright field micrograph (FIG. 4D) indicated that cells grown on native type I collagen containing 15 micrograms per milliliter of Tenascin C had beautiful collagen fibril alignment and normal cell morphology after the experimental methodology.

EXAMPLE 3

The objective of the experiment described in this Example was to ascertain whether cytochalasin D was able to enhance the cytoskeletal permissiveness of a cell for transfection with a nucleic acid, thereby resulting in an increase in the extent of transfection of cells provided cytochalasin D relative to cells which were not provided cytochalasin D. Cytochalasin D is an agent known to depolymerize F-Actin to G-Actin. The results of this experiment indicated that cytochalasin D itself was effective at enhancing the efficiency of delivery of a nucleic acid to a cell, thus increasing the extent of transfection.

A10 cells were grown on native type I collagen. The cells were transfected with p-EGFP-N3 (green fluorescent protein) plasmid DNA as described above. Immediately after lipofection, cytochalasin D at a final concentration of 1 nanomolar was either added to cells for thirty minutes, added to cells for an overnight incubation or not added at all (control). The fluorescence of control cells, cells treated with cytochalasin D for thirty minutes, and cells treated with cytochalasin D for an overnight incubation (FIGS. 6A, 6B and 6C, respectively) was assessed. Bright field micrographs were also taken of the control cells, cells treated with cytochalasin D for thirty minutes, and cells treated with cytochalasin D for an overnight incubation (FIGS. 7A, 7B and 7C, respectively).

As shown in FIG. 6, providing cytochalasin D to the cells grown on native type I collagen just after transfection resulted in a time-dependent increase in transfection of A10 cells, as evidenced by the time-dependent increase in GFP expression. Significantly greater transfection was exhibited by cells provided cytochalasin D, relative to cells which were not provided cytochalasin D. After just a thirty minute exposure to cytochalasin D, a marked change in cell shape was observed (FIG. 7), and increased transfection was exhibited relative to the control cells. Overnight exposure to cytochalasin D led to a more rounded cell shape and a notably higher amount of transfection. The results of this experiment indicated that forcing F-Actin depolymerization to G-Actin by providing cytochalasin D to cells just after lipofection was effective at enhancing the efficiency of delivery of a nucleic acid to a cell, thus increasing the extent of transfection.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for enhancing the efficiency of delivery of a nucleic acid to a cell in vitro, said method comprising
   a) providing to said cell a molecule which causes morphology of a cell to be transfected to change from a stellate morphology to an elongated morphology, said molecule being Tenacin C; and
   b) providing to said cell a nucleic acid encoding a heterologous protein or polypeptide for the transfection of said cell, whereby the presence of said molecule increases the efficiency of delivery of said nucleic acid to said cell when compared to cells transfected in the absence of said molecule.

2. The method of claim 1, wherein the nucleic acid encoding said heterologous protein or polypeptide is cloned in a vector which is provided to said cell simultaneously with providing said molecule.

3. The method of claim 1, wherein said nucleic acid encoding said heterologous protein or polypeptide is cloned in a vector which is provided to said cell prior to providing said molecule.

4. The method of claim 1, wherein said nucleic acid encoding said heterologous protein or polypeptide is cloned in a vector which is provided to said cell after providing said molecule.

5. A composition for enhancing the efficiency of delivery of a nucleic acid to a cell, said composition comprising
   a) tenascin C which causes the morphology of a cell to change from a stellate morphology to an elongated morphology; and
   b) a nucleic acid encoding a heterologous protein or polypeptide for the transfection of said cell.

6. The composition of claim 5, wherein said nucleic acid encoding said heterologous protein or polypeptide is cloned into a vector which is selected from the group consisting of a plasmid vector, a viral vector and a linearized nucleic acid.

7. A kit for enhancing the efficiency of delivery of a nucleic acid to a cell, said kit comprising
   a) an instructional material;
   b) tenascin C which causes morphology of a cell to change from a stellate morphology to an elongated morphology; and
   c) a nucleic acid encoding a heterologous protein or polypeptide for transfection into said cell.

8. The composition of claim 5, further comprising a vehicle that is suitable for pharmaceutical delivery.

9. The composition of claim 8, wherein said vehicle is a liposome forming lipid.

10. The composition according to claim 5, further comprising a polymeric carrier that permits controlled release of said molecule, said polymeric carrier being selected from the group consisting of controlled release film, nanoparticle, and microparticle.

* * * * *